United States Patent [19]

Higashide et al.

[11] 4,151,042
[45] Apr. 24, 1979

[54] METHOD FOR PRODUCING MAYTANSINOL AND ITS DERIVATIVES

[75] Inventors: Eiji Higashide, Takarazuka; Mitsuko Asai, Takatsuki; Seiichi Tanida, Kyoto, all of Japan

[73] Assignee: Takeda Chemical Industries, Ltd., Osaka, Japan

[21] Appl. No.: 811,442

[22] Filed: Jun. 29, 1977

[30] Foreign Application Priority Data

Mar. 31, 1977 [JP] Japan ................................ 52-37167
Apr. 1, 1977 [JP] Japan ................................ 52-37885

[51] Int. Cl.² .............................................. C12D 9/20
[52] U.S. Cl. ................................................... 195/96
[58] Field of Search ............................. 195/96, 80 R

[56] References Cited

U.S. PATENT DOCUMENTS 3,896,111  7/1975  Kupchan et al. ............... 260/239 T

OTHER PUBLICATIONS

Journal American Chemical Society, vol. 94, pp. 1354–1356.
Journal American Chemical Society, vol. 94, pp. 5294–5295.

Primary Examiner—Lionel M. Shapiro
Attorney, Agent, or Firm—Wenderoth, Lind & Ponack

[57] ABSTRACT

Maytansinol, maytanacine or maytansinol propionate is (are) produced by cultivating a microorganism belonging to the genus Nocardia and being capable of producing maytansinol, maytanacine or maytansinol propionate, causing the microorganism to accumulate maytansinol, maytanacine or maytansinol propionate and recovering the same.

Those compounds are useful for anti-tumor agents.

5 Claims, No Drawings

METHOD FOR PRODUCING MAYTANSINOL AND ITS DERIVATIVES

The present invention relates to a method for preparing maytansinol, maytanacine and maytansinol propionate which are anti-tumor agents.

It has been known that, among the above compounds, maytanacine and maytansinol propionate have strong anti-tumor activity [Kupchan et al.: Journal of the American Chemical Society 97, 5294 (1975)]. On the other hand, maytansinol itself has only weak anti-tumor activity (See the above reference) but it is a useful intermediate for easy preparation of maytanacine and maytansinol propionate and other various derivatives.

Maytansinol and maytanacine have been obtained by the above Kupchan et al. from bark of *Putterlickia verrucosa* (Plant belonging to the genus Maytenus) and thus yield is extremely low, such as 0.025 mg of the former compound and 0.36 mg of the latter from 1 kg of dried bark of the plant. As to maytansinol propionate, it has been obtained by chemical propionation of maytansinol.

The present inventors have collected various soil samples or the others and investigated antibiotics produced by microorganisms whcih are isolated from the samples, and these studies have reached findings that some of the microorganisms thus isolated can accumulate maytansinol, maytanacine or maytansinol propionate in the culture medium, these microorganisms belong to the genus Nocardia, and that these compounds can also be obtained by cultivating mutants derived from these microorganisms in a proper nutrient medium under appropriate conditions.

Further studies on the basis of these findings have now reached completion of the present invention.

Thus, the present invention relates to a method for preparing maytansinol, maytanacine or maytansinol propionate, which comprises cultivating a microorganism, which belongs to the genus Nocardia and is capable of producing maytansinol, maytanacine or maytansinol propionate, in a culture medium to accumulate maytansinol, maytanacine or maytansinol propionate in the cultured broth and recovering the same.

According to the prior art, the above compounds are obtainable from plants, but the plants are limited to specific ones, and great expense and a long period of time are required for the production at each stage of growth, felling, drying and pulverizing of the plants and extraction, separation and purification. Further, the yield is extremely low.

On the contrary, the processes of the present invention can be conducted easily and smoothly by cultivation of the microorganism, and a large amount of the objective compounds can be produced and obtained when desired.

The present invention is the first example of obtaining these compounds as metabolites of microorganisms, and can be said as an excellent method for preparation thereof.

As an example of the microorganism usable in the present method, there may be mentioned an actinomycete strain No. C-15003 which we isolated from soil and other samples in our screening for antibiotic-producing microorganisms.

The microbiological characters of Strain No. C-15003 were investigated by procedures analogous to those proposed by Schirling & Gottlieb [International Journal of Systematic Bacteriology 16, 313–340 (1966)].

The results of observations at 28° C. over 21 days are as follows.

(1) Morphological characters

The vegetative mycelium extends well and develops into branches, both on agar and in liquid medium. Many of the hyphae measure 0.8 to 1.2 μm in diameter and, in certain instances, may divide into fragments resembling rod bacteria or branched short lengths of hyphae. The strain gives good growth on various taxonomical media, with aerial mycelium being superimposed on the vegetative mycelium, although it frequently forms coremia like bodies (50–200×200–1000 μm) on which further aerial growth takes place. Many of the aerial mycelia are flexuous, straight or a loosely spiral like configuration being encountered on a few occasions. Microscopic examination of aged cultures reveals that only in few cases the conidia like cells occur in chains, while the cell suspensions obtained from the surfaces of such cultures, as microscopically examined, contained many elongated ellipsoidal (0.8–1.2 μm×4.8–6.8 μm) and ellipsoidal (0.8–1.2×1.0–2.0 μm) bodies resembling arthrospores.

Electron-microscopic examinations showed that these bodies had smooth surfaces.

(2) The constituents of cells

The strain was shake-cultured in modified ISP No. 1 medium at 28° C. for 66 to 90 hours, at the end of which time the cells were collected and rinsed. By the method of B. Becker et al. [Applied Microbiology 12, 421 (1964)] and the method of M. P. Lechevalier. [Journal of Laboratory and Clinical Medicine 71, 934 (1968)], the above whole cells were examined for diaminopimelic acid and sugar composition. The former was found to be the meso-form, while spots were detected, which corresponded to galactose and arabinose.

(3) Characteristics on taxonomical media

The strain showed comparatively good growth on various media, with the vegetative mycelium being colorless to pale yellow in initial phases of culture and light yellowish tan to yellowish tan in later phases. The strain produces soluble pigments, yellow to yellowish tan, in various taxonomical media. The aerial mycelium is powdery and generally gives moderate growth, being white to yellow or light yellowish tan. The characteristics of the strain in various taxonomical media are set forth in Table 1.

Table 1

| Cultural characteristics of Strain No. C-15003 on taxonomical media |
| --- |
| (A) Sucrose nitrate agar: <br>     Growth (G): Luxuriant, Brite Melon Yellow (3 ia)* to Amber (3 1c)*, coremia like bodies formed <br>     Aerial mycelium (AM): Scant, white <br>     Soluble pigment (SP): None or pale yellowish tan |
| (B) Glycerol nitrate agar: <br>     G : Moderate, Lt Ivory (2 ca)*, coremia like bodies formed <br>     AM: Moderate, white <br>     SP: None |
| (C) Glucose asparagine agar: <br>     G : Moderate, Brite Marigold (3 pa)* to Brite Yellow (2 pa)*. <br>     AM: Scant, white <br>     SP: Brite Yellow (2 pa)* |
| (D) Glycerol asparagine agar: <br>     G : Moderate, Lt Ivory (2 ca)*, coremia like bodies formed |

Table 1-continued
Cultural characteristics of Strain No. C-15003 on taxonomical media AM: Scant, white
    SP: None
(E) Starch agar:
    G : Moderate, Lt Ivory (2 ca)* to Lt Wheat
       (2 ea)*, coremia like bodies formed
    AM: Abundant, Lt Ivory (2 ca)*
    SP: None
(F) Nutrient agar:
    G : Moderate, Lt Ivory (2 ca)* to Colonial Yellow
       (2 ga)*, coremia like bodies formed
    AM: Scant, white
    SP: None
(G) Calcium malate agar:
    G : Moderate, Lt Ivory (2 ca)* to Lt wheat (2 ea)*,
       coremia like bodies formed.
    AM: Moderate, white to Lt Ivory (2 ca)*
    SP: None
(H) Yeast extract-malt extract agar:
    G : Moderate, Amber (3 1c)* to Brite Yellow
       (3 1a)*, coremia like bodies formed
    AM: Moderate, white to Lt Ivory (2 ca)*
    SP: None
(I) Oatmeal agar:
    G : Moderate, Lt Ivory (2 ca)* to Colonial Yellow
       (2 ga)*, coremia like bodies formed
    AM: Scant, white to light yellow
    SP: None
(J) Peptone yeast extract iron agar:
    G : Moderate, Colonial Yellow (2 ga)*
    AM: None
    SP: Colonial Yellow (2 ga)*
(K) Tyrosine agar:
    G : Moderate, Lt Ivory (2 ca)* to Lt Melon Yellow
       (3 ea)*, coremia like bodies formed
    AM: Moderate, white to Lt Ivory (2 ca)*
    SP: Camel (3 ie)*

*The color codes according to Color Harmony Manual, 4th ed. (Container Corporation of America, 1958)

(4) Physiological characters

The physiological characters of the strain are shown in Table 2. Temperature range for growth: 12° C. to 38° C. The temperature range in which good aerial growth occurs on agar (ISP No. 2) is 20° to 35° C.

Table 2
The physiological characters of Strain No. C-15003

| | |
|---|---|
| Temperature range for growth: | 12° to 38° C. |
| Temperature range for aerial growth: | 20° to 35° C. |
| Liquefaction of gelatin: | Positive |
| Hydrolysis of starch: | Positive |
| Reduction of nitrates: | Positive |
| Peptonization of milk: | Positive |
| Coagulation of milk: | Negative |
| Decomposition of casein: | Positive |
| Production of melanoid pigments: | Negative (peptone yeast extract iron agar), positive (tyrosine agar) |
| Decomposition of tyrosine: | Positive |
| Decomposition of xanthine: | Negative |
| Decomposition of hypoxanthine: | Negative |
| Tolerance to lysozyme: | Positive |
| Tolerance to sodium chloride: | 2% |

(5) Utilization of various carbon sources

The utilization of various carbon sources was investigated using a medium described in Pridham and Gottlieb [Journal of Bacteriology 56, 107 (1948)] and a basal medium of the same composition plus 0.1% of yeast extract. The resultant spectrum is shown in Table 3.

Table 3
The utilization of carbon sources by Strain No. C-15003

| Source of carbon | Growth | | Sources of carbon | Growth | |
|---|---|---|---|---|---|
| D-Xylose | + | ++* | Raffinose | ± | ±* |
| L-Arabinose | + | + | Melibiose | + | + |
| D-Glucose | ++ | ++ | i-Inositol | − | − |
| D-Galactose | + | + | D-Sorbitol | − | − |
| D-Fructose | +++ | ++ | D-Mannitol | ++ | ++ |
| L-Rhamnose | + | + | Glycerol | − | ± |
| D-Mannose | +++ | ++ | Soluble starch | + | + |
| Sucrose | ++ | ++ | Control | − | − |
| Lactose | − | −* | | | |
| Maltose | ± | + | | | |
| Trehalose | + | ++ | | | |

*Basal medium with 0.1% yeast extract added
Note:
+++: Luxuriant growth
++: Good growth
+: Growth
±: Poor growth
−: No growth

(6) Other characteristics

The cells were harvested by the procedure previously described in (2) and DNA was prepared by a procedure analogous to that of J. Marmur et al. [Journal of Molecular Biology, 3,208, 1961]. The G-C(Guanine-Cytosine) content of the DNA was found to be about 71 mole %.

Gram-staining of the vegetative mycelium of this strain was positive.

The above characteristics of Strain No. C-15003 were compared with the descriptions in S. A. Waksman's "The Actinomycetes Vol. 2" [The Williams and Wilkins Co., 1961]; R. E. Buchanan and N. E. Gibbons, "Bergey's Manual of Determinative Bacteriology, 8th ed, 1974;" and other literatures.

Whilst this strain was thought to belong to Group III of the genus Nocardia, the failure to find any species having the characters so far described among the known strains led us to conclude that this strain represented a novel species of microorganism.

The present Strain No. C-15003 has been deposited at Fermentation Research Institute, Agency of Industrial Science and Technology (FERM) under the receipt number of 3992 and at Institute for Fermentation, Osaka (IFO) under the accession number of IFO 13726 and at The American Type Culture Collection (ATCC), Maryland, U.S.A. under the accession number of 31281.

While Strain No. C-15003 is a novel species of the genus Nocardia as just mentioned, it is liable, as are microorganisms generally, to undergo variations and mutations, whether spontaneously or under the influence of a mutagen. For example, the many variants of the strain which are obtainable by irradiation with X-rays, gamma rays, ultraviolet light, etc., by monocell isolation, by culture on media containing various chemicals, or by any other mutagenic treatment, as well as the mutants spontaneously derived from the strain, should not be substantially considered to represent any other distinct species but, rather, any of such variants and mutants capable of elaborating maytansinol, maytanacine and maytansinol propionate may be invariably utilized for the purposes of this invention as the strain No. C-15003. By way of example, subjecting Strain No. C-15003 to various mutagenic treatments yields mutants substantially lacking the ability to produce soluble pigments, mutants with substrate mycelia which are colorless, yellowish green, reddish tan or orange red, mutants whose hyphae are ready to fragment into bacillary elements or branched short hyphal fragments, and mutants with abundant white aerial mycelia or substantially without aerial mycelia.

The medium employed for the cultivation of strain capable of producing maytansinol, maytanacine or maytansinol propionate (hereinafter, sometimes abbreviated as "producible strain") may be whichever of a liquid and a solid medium only if it contains nutrients which the strain may utilize, although a liquid medium is preferred for high-production runs. The medium may comprise carbon and nitrogen sources which Strain No. C-15003 may assimilate and digest, inorganic matter, trace nutrients, etc. As examples of said carbon sources may be mentioned glucose, lactose, sucrose, maltose, dextrin, starch, glycerol, mannitol, sorbitol, etc., fats and oils (e.g. soybean oil, lard oil, chicken oil, etc.) and so forth. The nitrogen sources may for example be meat extract, yeast extract, dried yeast, soybean meal, corn steep liquor, peptone, casein, cottonseed flour, spent molasses, urea, ammonium salts (e.g. ammonium sulfate, ammonium chloride, ammonium nitrate, ammonium acetate, etc.) and so forth. The medium may further contain salts of sodium, potassium, calcium, magnesium, etc., salts of iron, manganese, zinc, cobalt, nickel, etc., salts of phosphoric acid, boric acid, etc. and organic acid salts such as acetates and propionates. Further, the medium may contain, as added, various amino acids (e.g. glutamic acid, aspartic acid, alanine, glycine, lysine, methionine, proline, etc.), peptides (e.g. dipeptides, tripeptides, etc.), vitamines (e.g. $B_1$, $B_2$, nicotinic acid, $B_{12}$, C, E, etc.), nucleic acids (e.g. purine, pyrimidine and derivatives thereof and so forth. For the purpose of adjusting the pH of the medium, there may be added an inorganic or organic acid, alkali, buffer or the like. Suitable amounts of oils, fats, surfactants, etc. may also be added as antifoams.

The cultivation may be conducted by any of the stationary, shake, submerged aerobic and other cultural conditions. For high production runs, submerged aerobic culture is of course preferred. While the conditions of culture, of course, depends upon the condition and composition of medium, the strain, cultural method and other factors, it is normally preferred to carry out incubation at 20° to 35° C. with an initial pH of about 7.0 or thereabouts. Particularly desirable is a temperature from 23° to 30° C. in an intermediate stage of cultivation, with an initial pH of 6.5 to 7.5. While the incubation time also is variable according to the same factors as mentioned above, it is advisable to continue the incubation until the titer of the desired antibiotic product becomes maximal. In the case of shake culture or aerobic submerged culture in liquid medium, the time required normally ranges from about 48 to 144 hours.

The potency of the antibiotic was assayed with *Tetrahymena pyriformis* W as an assay organism. Thus, the above microorganism was grown on a test medium [20 g of Proteose-peptone (Difco), 1 g of yeast extract (Difco), 2 g of glucose, 1000 ml of distilled water and 10 ml of 1 M-phosphate buffer (pH 7.0)] at 28° C. for 44 to 48 hours and the potency of the antibiotic was determined by the serial dilution method with a monitoring of the turbidity of growth and by a thin-layer chromatographic (briefly, TLC) assay to be described hereinafter.

Maytanacine, maytansinol propionate or maytansinol is produced and accumulated in the resultant cultured broth, both extracellularly and intracellularly.

None of these substances shows distinct antibiotic activity, and thus they have been detected by TLC which is set forth in parallel to detection by activity to the Tetrahymena strain. Thus, the fermentation broth is separated into cells and filtrate by filtration or centrifugation and the filtrate is extracted with the same volume of ethyl acetate. To the cells is added the same amount of 70% acetone-water as the filtrate and, after an hour's stirring at 20° C., the suspension is filtered. The acetone is removed from the filtrate and the resultant aqueous filtrate is extracted with ethyl acetate. Each of the extracts is concentrated to 1/100 by volume and subjected to thin-layer chromatography on a silica gel-glass plate (Merck, West Germany, Kieselgel 60 $F_{254}$, 0.25 mm, 20×20) (solvent system:chloroform-methanol=9:1). The potency was determined on the basis of the intensity of spots detected by irradiation with ultraviolet light at 2537 Å.

Maytanacine, maytansinol propionate or maytansinol which is thus produced in the cultured broth, are lipophyl and neutral, they can be conveniently recovered by separation and purification procedures which are normally employed for the harvest of such microbial metabolites. For example, there may be employed a procedure which utilizes the difference in solubility between the antibiotic and impurity, means which utilizes the fractionating adsorptive affinity of various adsorbents such as activated carbon, macroporous nonionic resins, silica gel, alumina, etc., a procedure of removing the impurities by means of ion exchange resins, and so forth, as applied singly or in a suitable combination or as applied in repetition.

Since, as aforesaid, maytanacine, maytansinol propionate or maytansinol occur in both the filtrate and cells, the antibiotics are separated and purified by means of such an adsorbent, if one is employed, either directly or after a solvent extraction in the case of the filtrate, or after a solvent extraction in the case of microbial cells. The solvent extraction may be performed by any of the following and other methods e.g. (1) solvent extraction from the culture broth prior to separation of cells and (2) solvent extraction of the cells and the filtrate obtained by filtration, centrifugation or other process. To extract the filtrate and cells independently, the following procedure may be taken advantageously.

The solvents suitable for extraction of the filtrate are water-immiscible organic solvents such as fatty acid esters, e.g. ethyl acetate and amyl acetate; alcohols, e.g. butanol; halogenated hydrocarbons, e.g. chloroform; and ketones, e.g. methyl isobutyl ketone. The extraction is carried out at a pH near neutral and, preferably, the culture fluid previously adjusted to pH 7 is extracted with ethyl acetate. The extract is washed with water and concentrated under reduced pressure. Then, a nonpolar solvent such as petroleum ether or hexane is added to the concentrate and the crude product I containing the active compound is recovered. Because, on TLC, a number of spots are detected other than maytanacine, maytansinol propionate or maytansinol, the product I is sequentially subjected to the following purification procedures. Thus, a routine purification procedure, particularly adsorption chromatography is useful and, for this purpose, one of those common adsorbents such as silica gel, alumina, macroporous nonionic adsorbent resin, etc. may be employed. For purification from the crude product I, silica gel is most useful. And development may be carried out, for example starting with petroleum ether and hexane and elution is performed by the addition of a polar solvent such as ethyl acetate, acetone, ethanol or methanol. In a typical process, using silica gel (Merck, West Germany, 0.05-0.2 mm) as a carrier, column chromatography is carried out with a serial increase in the hexane to ethyl acetate ratio. The eluate is sampled and investigated by TLC and the fractions containing effective ingredients are pooled and concentrated under reduced pressure. Then, petroleum ether or hexane is added to the concentrate, whereby the crude product II is obtained. Since this product still contains impurities, it is further purified as follows. For example, the product II may be purified by means of a second silica gel column using a different solvent system. The developing system for this purpose may consist in a halogenated hydrocarbon such as dichloromethane or chloroform, with the addition of polar solvent such as an alcohol, e.g. ethanol or methanol, a ketone, e.g. acetone or methyl ethyl ketone, or the like. In this way, maytanacine, maytansinol propionate or maytansinol is isolated. The order of solvent systems for the first and second silica gel columns may be reversed and, in addition, ordinary organic solvents may be used in conjunction with the above systems if necessary.

Where a macroporous adsorbent resin is used as purification means for crude product II, elution of maytanacine, maytansinol propionate or maytansinol is accomplished with a mixture of water with a lower alcohol, a lower ketone or an ester. The lower alcohol may for example be methanol, ethanol, propanol or butanol and the lower ketone may for example be acetone or methyl ethyl ketone. The ester may for example be ethyl acetate. In a typical procedure, the crude product II is dissolved in 60% methanol-water and adsorbed on a column of Diaion HP-10 (Mitsubishi Kasei K.K.). The column is washed with 70% methanol-water and, then, elution is carried out with 90% methanol-water. In this way, maytanacine, maytansinol propionate or maytansinol is eluted from the column.

In either of the processes described above, the fractions containing the object components are pooled and concentrated under reduced pressure. To the dry product is added 5 to 8 volumes of ethyl acetate and the mixture is allowed to stand, whereupon crystals of maytanacine, maytansinol propionate or maytansinol separate, respectively. When the crystals contain maytanacine and maytansinol propionate, they are then separated from each other by means of an adsorbent such as those mentioned hereinbefore. Thus, using silica gel or a macroporous nonionic adsorbent resin and the above solvents, the desired compounds may be fractionally eluted. When, for example, silica gel is employed, development is carried out with hexane, ethyl acetate, or chloroform-methanol, whereby maytansinol propionate and maytanacine emerge in that order. After detection by TLC, the fractions are respectively concentrated under reduced pressure and ethyl acetate is added to the concentrates. In this manner, the respective compounds can be obtained as crystals. When a macroporous nonionic adsorbent resin is employed, gradient elution with a varying ratio of alcohol, ketone or ester to water may be utilized. For example, by the gradient elution method involving the use of 60% methanol-water and 95% methanol-water, with 5% sodium chloride added, maytanacine and maytansinol propionate emerge in the order mentioned. After sampling and detection by TLC, each group of active fractions is concentrated under reduced pressure and crystallized from ethyl acetate. The isolated crystals include ethyl acetate as a solvent of crystallization and, after drying over phosphorus pentoxide at 70° C. for 8 hours, show the following physical and chemical properties. (Table 4)

Table 4

|  | Maytanacine $C_{30}H_{39}ClN_2O_9$ | Maytansinol propionate $C_{31}H_{41}ClN_2O_9$ | Maytansinol $C_{28}H_{37}ClN_2O_8$ |
|---|---|---|---|
| Melting point (° C.) | 235°-236° | 188°-190° | 172.5°-174° |
| Specific rotation | $[\alpha]_D^{22°}$-121°±10° (C=0.25,CHCl$_3$) | $[\alpha]_D^{22°}$-127°±10° (C=0.35,CHCl$_3$) | $[\alpha]_D^{22°}$-313°±10° (C=0.22,CHCl$_3$) |
| Analysis Found (%) | C 59.62<br>H 6.93<br>N 4.28<br>Cl 5.74 | 59.93<br>6.82<br>4.32<br>5.57 | 59.28<br>6.38<br>5.02<br>6.15 |
| Analysis Calcd. (%) | C 59.85<br>H 6.48<br>N 4.61<br>Cl 5.84 | 59.94<br>6.65<br>4.51<br>5.71 | 59.52<br>6.60<br>4.96<br>6.27 |
| Ultraviolet absorption spectrum nm($\epsilon$) | 233(30330)<br>240(sh.28240)<br>252(27850)<br>280(5680)<br>288(5660) | 233(30240)<br>240(sh.28400)<br>252(27650)<br>280(5740)<br>288(5710) | 232(32750)<br>244(sh.30850)<br>252(31650)<br>281(5750)<br>288(5700) |
| Infrared absorption spectrum (cm$^{-1}$) | 1740,1730,1670<br>1580 | 1740,1730,1670,<br>1580 | 1715,1670,1580 |
| Mass spectrum (m/e) | 545,485,470,450 | 559,485,470,450 | 503,485,470,450 |
| Acid, neutral or basic | lipophyl and neutral substance | lipophyl and neutral substance | lipophyl and neutral substance |
| Color reactions | Dragendorff reaction: positive<br>Beilstein reaction: | Dragendorff reaction: positive<br>Beilstein reaction: | Dragendorff reaction: positive<br>Beilstein reaction: |

Table 4-continued

| Maytanacine $C_{30}H_{39}ClN_2O_9$ | Maytansinol propionate $C_{31}H_{41}ClN_2O_9$ | Maytansinol $C_{28}H_{37}ClN_2O_8$ |
|---|---|---|
| positive | positive | positve |

Above mentioned data of elemental analysis, specific rotation, UV spectra, IR spectra, mass spectra, etc. are in good agreement with the data of maytanacine, maytansinol propionate and maytansinol which are given in the literature Kupchan et al. (The Journal of American Chemical Society 97, 5294 (1975).

The following examples are further illustrative but by no means limitative of the invention, wherein "part(s)" is based on weight unless otherwise noted and the relationship between "part(s)" and "part(s) by volume" corresponds to that between "gram(s)" and "milliliter(s)", and "%" is based on "weight/volume" unless otherwise noted.

EXAMPLE 1

Maytansinol-, maytanacine- and maytansinol propionate-producible Nocardia No. C-15003 (IFO 13726; FERM 3992; ATCC 31281) as grown on a medium (yeast extract-malt extract agar) was used to inoculate a 200 parts by volume fermenter containing 40 parts by volume of a seed culture medium (2% glucose, 3% soluble starch, 1% raw soybean meal, 1% corn steep liquor, 0.5% Polypepton, 0.3% NaCl, 0.5% CaCO$_3$, pH 7.0). The inoculated medium was incubated at 28° C. for 48 hours to obtain an inoculum. A 0.5 part by volume portion of the inoculum thus obtained was transferred to a 200 parts by volume fermenter containing 40 parts by volume of a fermentation medium composed of 5% dextrin, 3% corn steep liquor, 0.1% Polypepton and 0.5% CaCO$_3$ (pH 7.0), and cultivated at 28° C. for 90 hours to give inoculum (seed culture).

As determined by the serial dilution method using *Tetrahymena pyriformis* W as an assay organism and maytansinol propionate as the standard product, the above culture was found to have a titer of 25 μg/ml.

EXAMPLE 2

A 10 parts by volume portion of the inoculum (seed) obtained in Example 1 was transferred to a 2000 parts by volume fermenter containing 500 parts by volume of a seed culture medium (same as above) and incubated at 28° C. for 48 hours. A 500 parts by volume portion of the resultant culture was transferred to a 50000 parts by volume tank of stainless steel containing 30000 parts by volume of seed culture medium and cultivated at 28° C. under aeration (30000 parts by volume/min.), agitation [280 r.p.m. (½ DT)] and internal pressure (1 kg/cm$^2$) to obtain a seed culture. This culture was used to seed a 200000 parts by volume tank of stainless steel containing 100000 parts by volume of a fermentation medium similar to the one used in Example 1 at an inoculation rate of 10%. The inoculated medium was incubated at 28° C. under aeration (100000 parts by volume/min.), agitation [200 r.p.m. (¼ DT)] and internal pressure (1 kg/cm$^2$) for 90 hours. As determined by the same procedure as that described in Example 1, the culture obtained above was found to have a titer of 25 μg/ml.

To 90000 parts by volume of the culture obtained above was added 2000 parts of Hyflo-supercel ® (Johnes and Manville Products, U.S.A.) and, after thorough mixing, the mixture was filtered on a pressure filter to obtain 85,000 parts by volume of filtrate and 32,000 parts of moist cells. The filtrate (85,000 parts by volume) was stirred and extracted with 30,000 parts by volume of ethyl acetate. This procedure was repeated once again. The ethyl acetate layers were pooled, washed twice with 30,000 parts by volume portions of water, dried by the addition of 500 parts of anhydrous sodium sulfate and concentrated under reduced pressure to 200 parts by volume. Petroleum ether was added to the concentrate and the resultant precipitate was recovered by filtration (53 parts). This crude product I was stirred with 100 parts by volume of ethyl acetate and the insolubles were filtered off. The filtrate was stirred with 10 parts of silica gel (Merck, West Germany, 0.05–0.2 mm) and the ethyl acetate was removed under reduced pressure. The residue was applied to the top of a silica gel column (400 parts by volume). Elution was carried out with 500 parts by volume of hexane, 500 parts by volume of hexane-ethyl acetate (3:1), 500 parts by volume of hexane-ethyl acetate (1:1), 500 parts by volume of hexane-ethyl acetate (1:3), 500 parts by volume of ethyl acetate and 1000 parts by volume of ethyl acetate-methanol (50:1), and 1000 parts by volume of ethyl acetate-methanol (25:1), with the eluate being collected in 100 parts by volume fractions.

One part by volume portion of each fraction was concentrated to dryness, and 0.1 part by volume of ethyl acetate was added to the concentrate. The mixture was spotteed at 2.5 cm from the bottom edge of a silica gel-glass plate (Merck, West Germany, 60 F$_{254}$, 0.25 mm, 20×20) and developed for about 17 cm with a solvent system of ethyl acetate-methanol (19:1). After development, detection was carried out with ultraviolet light (2537 Å).

The active fractions No. 25–30 of Rf 0.58–0.63 and the fractions No. 38–40 of Rf 0.25–0.30 were collected and concentrated under reduced pressure to about 20 parts by volume, respectively. To these concentrates were added each 150 parts by volume of petroleum ether to obtain 5 parts of a crude product II and 2 parts of crude maytansinol.

In 10 parts by volume of ethyl acetate was dissolved 0.5 part of the crude product II obtained above and the solution was stirred well with 4 parts of silica gel (Merck, West Germany, 0.05–0.2 mm). The ethyl acetate was removed under reduced pressure. The residue was applied to the top of a column of 300 parts by volume silica gel and the column was first washed with 500 parts by volume of chloroform and then eluted with 500 parts by volume of chloroform-methanol (50:1), 500 parts by volume of chloroform-methanol (20:1) and 500 parts by volume of chloroform-methanol (10:1). The eluate was collected in 25 parts by volume fractions.

A 0.5 part by volume portion of each fraction was concentrated under reduced pressure. To the concentrate was added 0.05 part by volume of ethyl acetate, and the mixture as a sample was subjected to thin layer chromatography (developing system: chloroform-methanol=9:1).

The fraction Nos. 40 and 41 absorbing at 2537 Å in the zone of Rf 0.48–0.50 were collected and concentrated to dryness under reduced pressure. To the residue was added 0.5 part by volume of ethyl acetate and the mixture was allowed to stand, whereupon 0.05 part mixed crystals of maytanacine and maytansinol propionate were obtained.

0.05 part of the above mixed crystals of maytanacine and maytansinol propionate was dissolved in 5 parts by volume of methanol, followed by addition of 0.1 part of sodium chloride and 5 parts by volume of water. A column was packed with 200 parts by volume of Diaion HP-10 (Mitsubishi Kasei K.K.) and washed with 600 parts by volume of 50% methanol-water containing 5% of NaCl. The sample solution prepared above was passed through the column, and gradient elution was carried out using 1500 parts by volume of 60% methanol-water containing 5% NaCl and 1500 parts by volume of 95% methanol-water. The eluate was collected in 15 parts by volume fractions and each fraction was investigated by thin layer chromatography. The fractions 130 to 135 contained maytanacine, and the fractions 138–142 contained maytansinol propionate.

Each group of fractions was concentrated and dissolved by the addition of 30 ml of water and 50 ml of ethyl acetate. The solution was shaken in a separatory funnel and the water layer was separated and, after washing twice with 30 ml-portions of water, the ethyl acetate layer was dried over anhydrous sodium sulfate, concentrated and allowed to stand. In the above manner, crystals were obtained from each group of fractions. The crystals were collected by filtration and dried. Maytanacine 0.013 part. Maytansinol propionate 0.025 part.

In 3 parts by volume of ethyl acetate was dissolved 0.2 part of the crude maytansinol obtained above and the solution was stirred well with 0.5 part of silica gel (Merck, West Germany, 0.05–0.2 mm). The ethyl acetate was removed under reduced pressure. The residue was applied to the top of a column of 80 parts by volume silica gel and the column was first washed with 150 parts by volume of chloroform and then eluted with 150 parts by volume of chloroform-methanol (50:1), 150 parts by volume of chloroform-methanol (20:1) and 300 parts by volume of chloroform-methanol (10:1). The eluate was collected in 10 parts by volume fractions.

A 0.5 parts by volume portion of each fraction was concentrated under reduced pressure. To the concentrate was added 0.05 part by volume of ethyl acetate, and the mixture as a sample was subjected to thin layer chromatography (developing system: chloroform-methanol=9:1).

The fraction Nos. 50 to 52 absorbing at 2537 Å in the zone of Rf 0.33 to 0.38 were collected and concentrated to dryness under reduced pressure. To the residue was added 0.5 part by volume of ethyl acetate and the mixture was allowed to stand, whereupon 0.020 part crystals of maytansinol were obtained.

EXAMPLE 3

With stirring, 32000 parts of the cells obtained in Example 2 were extracted with 50,000 parts by volume of 70% acetone-water for 3 hours and, then, filtered on a pressure filter. The extraction with 50,000 parts by volume of 70% acetone-water and subsequent filtration was repeated once again. The filtrates were pooled and the acetone was removed by concentration under reduced pressure. The resultant aqueous system was passed through a column of 5000 parts by volume Diaion HP-10 (Mitsubishi Kasei K.K.). The column was washed with 20000 parts by volume of water and 50% aqueous methanol, followed by elution with 15000 parts by volume of 90% methanol-water. The eluate was concentrated under reduced pressure to 3000 parts by volume and shaken with 3000 parts by volume of water and 3000 parts by volume of ethyl acetate. The above procedure was repeated once again. The ethyl acetate layers were combined, washed with water, dried by the addition of anhydrous sodium sulfate and concentrated under reduced pressure to 200 parts by volume. Following the addition of petroleum ether, the precipitate was recovered by filtration (280 parts). The above-obtained crude product I was purified by means of a column of silica gel similarly to Example 1 to recover 1.0 part of crude product II and 0.5 part of crude maytansinol.

EXAMPLE 4

1000 Parts by volume of the culture of Example 2 was inoculated into a 200,000 parts by volume tank of stainless steel containing 100,000 parts by volume of a seed culture medium and the inoculated medium was incubated at 28° C. under aeration (100,000 parts by volume/min.) and agitation (200 r.p.m.) for 48 hours to prepare a seed culture. This seed culture was transferred to a 2,000,000 parts by volume tank of stainless steel containing 1,000,000 parts by volume of a fermentation medium as same as that used in Example 1 at a transplantation rate of 10%. Cultivation was carried out at 28° C. under aeration (1,000,000 parts by volume/min.), agitation [120 r.p.m. (1/3 DT)] and internal pressure (1 kg/cm$^2$) for 90 hours. The resultant culture was found to have a titer of 20 $\mu$g/ml as assayed by the assay procedure described in Example 1. To 900,000 parts by volume of the above-obtained culture was added 900,000 parts by volume of acetone and, after an hour's stirring, 20000 parts of Hyflo-Supercel (Johnes & Manville, U.S.A.), was added. The mixture was further stirred and filtered on a pressure filter machine. To 1,700,000 parts by volume of the resultant filtrate was added 500,000 parts by volume of water and, in a Podbielniak (Podbielniak, Inc., U.S.A.), the mixture was extracted with 1,000,000 parts by volume of ethyl acetate. The ethyl acetate layer was washed with water, dried by the addition of anhydrous sodium sulfate and concentrated under reduced pressure. To the concentration was added petroleum ether and the resultant precipitate was recovered by filtration and dried. By the above procedure was obtained 680 parts of crude product I. Thereafter, as in Examples 2 and 3, this crude product was purified to obtain 1.1 parts of maytanacine, 2.2 parts of maytansinol propionate, and 0.1 part of maytansinol.

What we claim is:

1. A method for preparing maytansinol, maytanacine or maytansinol propionate which comprises cultivating a microorganism belonging to the genus Nocardia and being capable of producing maytansinol, maytanacine or maytansinol propionate in a culture medium containing assimilable carbon sources and digestible nitrogen sources until maytansinol, maytanacine or maytansinol propionate is substantially accumulated therein, and recovering the same.

2. A method as claimed in claim 1, wherein the product obtained is maytansinol.

3. A method as claimed in claim 1, wherein the product obtained is maytanacine.

4. A method as claimed in claim 1, wherein the product obtained is maytansinol propionate.

5. A method as claimed in claim 1, wherein the microorganism is Nocardia No. C-15003 (ATCC 31281; IFO 13726; FERM 3992) or its mutants or variants thereof.

* * * * *